United States Patent [19]

Carr et al.

[11] Patent Number: 5,093,341
[45] Date of Patent: Mar. 3, 1992

[54] N-ARALKYL PIPERIDINE DERIVATIVES USEFUL AS ANTITHROMBOLYTIC AGENTS

[75] Inventors: Albert A. Carr; John E. Koerner; Richard C. Dage; Tung Li, all of Cincinnati; Francis P. Miller, Loveland, all of Ohio

[73] Assignee: Merrell Dow Pharmaceuticals Inc., Cincinnati, Ohio

[21] Appl. No.: 237,600

[22] Filed: Aug. 26, 1988

Related U.S. Application Data

[63] Continuation-in-part of Ser. No. 134,406, Dec. 17, 1987, abandoned.

[51] Int. Cl.$^5$ .......................................... A61K 31/445
[52] U.S. Cl. ................................ 514/321; 514/330; 514/331; 546/197; 546/225; 546/232; 546/234
[58] Field of Search ..................... 514/321, 330, 331

[56] References Cited

U.S. PATENT DOCUMENTS 4,711,899 12/1987 Gaudilliere et al. ............... 514/330
4,783,471 11/1988 Carr et al. .......................... 514/331

FOREIGN PATENT DOCUMENTS 0235752 9/1987 European Pat. Off. .

Primary Examiner—Mukund J. Shah
Assistant Examiner—Philip F. Datlow
Attorney, Agent, or Firm—William J. Stein

[57] ABSTRACT

The present invention is directed to a new class of compounds useful as antiarrhythmics, analgesics and serotonin 5HT$_2$ antagonists, which compounds have the following formula:

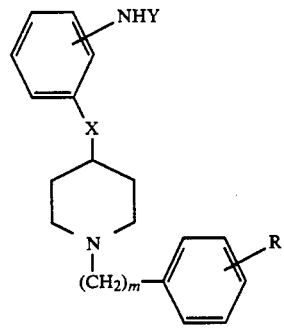

wherein; Y is represented by H, $CO(CH_2)_nCH_3$ in which n is an integer from 0–3, or $SO_2(CH_2)_nCH_3$ in which n is an integer from 0—3; X is represented CO, CHOH, or C=N—O—A, wherein A is represented by hydrogen or a $C_{1-4}$ alkyl; R is either selected from the group consisting of halogens, lower alkyl groups, lower alkoxy groups, and hydrogen or R is a divalent substituent and is represented by a 3,4-methylenedioxy or a 3,4-ethylenedioxy substituent; m is an integer from 1–5; and the pharmaceutically acceptable acid addition salts thereof.

6 Claims, No Drawings

N-ARALKYL PIPERIDINE DERIVATIVES USEFUL AS ANTITHROMBOLYTIC AGENTS

This is a continuation in part of Ser. No. 134,406, Filed Dec. 17, 1987.

The present invention relates to novel 1,4-disubstituted piperidinyl pharmaceutical compounds. Another aspect of the invention pertains to methods for treating various disease states. A further aspect of the present invention relates to novel intermediate compounds useful in synthesizing said pharmaceutical compounds.

In accordance with the present invention, a new class of therapeutic agents have been discovered which can be represented by the formula:

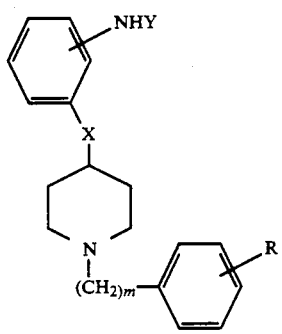

Formula I wherein; Y is represented by H, $CO(CH_2)_nCH_3$ in which n is an integer from 0-3, or $SO_2(CH_2)_nCH_3$ in which n is an integer from 0-3; X is represented CO, CHOH, or C=N—O—A, wherein A is represented by hydrogen or a $C_{1-4}$ alkyl; R is either selected from the group consisting of halogens, lower alkyl groups, lower alkoxy groups, and hydrogen or R is a divalent substituent and is represented by a 3,4-methylenedioxy or a 3,4-ethylenedioxy group; m is an integer from 1-5; and the pharmaceutically acceptable acid addition salts thereof.

These compounds have a number of therapeutic indications. They are Class III antiarrhythmic agents, and non-narcotic analgesics. They are also serotonin $5HT_2$ antagonists and thus are useful for treating a number of disease states.

As used in this application:

a) the term halogen refers to a fluorine, chlorine, or bromine atom;

b) the term lower alkyl group refers to a branched or straight chained alkyl group containing from 1-4 carbon atoms, such as methyl, ethyl, n-propyl, isopropyl, n-butyl and isobutyl;

c) the term lower alkoxy group refers to a straight or branched alkoxy group containing from 1-4 carbon atoms, such as methoxy, ethoxy, n-propoxy, isopropoxy, n-butoxy and isobutoxy;

d) the term carbonyl refers to a substituent having the following structure:

e) the term hydroxymethyl group refers to the following substituent, —CHOH—;

f) the term oxime refers to a substituent having the following structure:

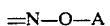

wherein A is represented by hydrogen or a $C_{1-4}$ alkyl;

g) the term 3,4-methylenedioxy or 3,4-ethylenedioxy refers to the following substituent:

wherein e equals 1 or 2.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methane sulfonic acid and 2-hydroxyethane sulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art.

In the compounds of Formula I in which R is represented by a monovalent substituent, there can be up to 3 such substituents occurring on the indicated phenyl ring. These substituents can be located at any of positions 2-6 of the indicated phenyl ring. These substituents can be the same or can differ from one another. When R is represented by a divalent substituent (i.e. 3,4-methylene or ethylene dioxy), then the indicated phenyl ring should not be substituted with any other substituents and the divalent substitution should appear at the 3 and 4 positions of the phenyl ring. The amino group which is represented by NHY, can be located at either of positions 2 or 4 of the indicated phenyl ring.

Representative examples of preferred compounds encompassed by Formula I are those selected from the group consisting of:
1) N-[4-[[1-(2-phenylethyl)-4-piperidinyl]carbonyl]-phenyl]-acetamide,
2) N-[4[hydroxy[1-(2-phenylethyl)-4-piperidinyl]methyl]-phenyl]-acetamide,
3) N-[4-[hydroxy[1-(2-phenylethyl)-4-piperidinyl]methyl]phenyl]-methanesulfonamide,
4) N-[4-[[1-(2-phenylethyl)-4-piperidinyl]carbonyl]-phenyl]-methanesulfonamide,
5) N-[4-[[1-[2-(4-methoxyphenyl)ethyl]-4-piperidinyl]-carbonyl]phenyl]-methanesulfonamide, 6) N-[4-[[1-[2-(4-fluorophenyl)ethyl]-4-piperidinyl]-carbonyl]phenyl]-methanesulfonamide,
7) N-[4-(hydroxy-[1-[2-(4-methoxyphenyl)ethyl]-4-piperidinyl]ethyl]phenyl]-methanesulfonamide,
8) N-[4-[hydroxy-[1-[2-(4-fluorophenyl)ethyl]-4-piperidinyl]methyl]phenyl]-methanesulfonamide,
9) N-[4-[[1-2-(3,4-methylenedioxyphenyl)-ethyl]-4-piperidinyl]carbonyl]phenyl-methanesulfonamide,
10) N-[4-[hydroxy-[1-[2-(3,4-methylenedioxy-phenyl)ethyl]-4-piperidinyl]methyl]phenyl]-methanesulfonamide,
11) N-[4-[(methoxyimino)[1-(2-phenylethyl)-4-piperidinyl]methyl]phenyl-methanesulfonamide,
12) 4-aminophenyl[1-(2-phenylethyl)-4-piperidinyl]methanone,
13) and the pharmaceutically acceptable acid addition salts thereof.

The most preferred compounds of Formula I are those wherein; R is represented by at least one methoxy substitient, preferably 2; m is 2; n is 0; and the amino grouping is located at the 4-position on the indicated phenyl ring.

The compounds of Formula I can be synthesized by techniques known in the art. It is currently preferred that the compounds be synthesized in the following novel manner.

If the desired compound is substituted with a carbonyl function at the 4-position of the piperidinyl ring (i.e., in Formula I, X is CO), then the following synthesis is currently preferred.

A Friedel-Crafts acylation should be conducted with starting materials which can be described by the following formulae:

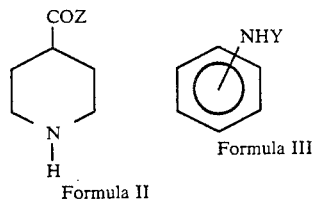

Formula II       Formula III wherein Y is as defined in Formula I, and Z is selected from Br, Cl, I or F. The compound of Formula II is generally present as an acid addition salt.

This Friedel-Crafts acylation produces a novel intermediate of the Formula:

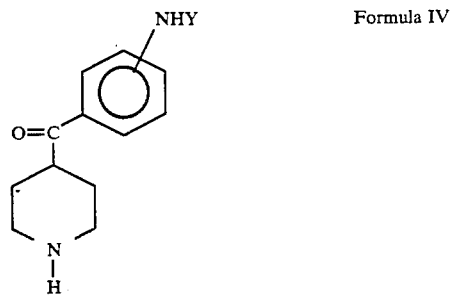

Formula IV wherein Y is as defined in Formula I.

The amino-substituted-phenyl compound (compound represented by Formula III) utilized as a starting material should correspond structurally to its analogous counterpart in the desired 4-substituted piperidinyl intermediate since all of its substituents will be retained in the intermediate and ultimately the final product.

Likewise, the 4-halo-carbonyl-piperidine utilized as the starting material (compound represented by Formula II) should correspond structurally to its counterpart in the desired 4-substituted piperidinyl intermediate since any substituents appearing on the piperidinyl ring will be retained in the intermediate as well as the final product (with the exception of the 4-halo substituent). Therefore, the piperidinyl ring of the 4-halo-carbonyl-piperidinyl compound should not be substituted with any functional groups at the 1, 2, 3, 5, or 6 positions since they would be retained in the final product.

For example if the desired 1,4-disubstituted piperidinyl compound is N-[4-[[1-(2-phenylethyl)-4-piperidinyl]-carbonyl]phenyl]-acetamide, then its intermediate, N-[4-(4-piperidinyl-carbonyl)phenyl]acetamide can be produced by reacting, a 4-halo-carbonyl-piperidine, with acetanilide.

It is currently preferred that approximately equimolar quantities of the amino-substituted phenyl compound and the 4-halo-carbonyl-piperidine be reacted together. A slight excess of either reactant will not be deleterious to the reaction.

The reaction can be conducted with Friedel-Crafts catalysts known in the art, such as, for example, $AlCl_3$, $ZnCl_2$, $AlBr_3$, $SnCl_4$, etc. $AlCl_3$ is currently utilized.

The Friedel-Crafts catalyst is generally present in the reaction zone in a quantity of from 1–4 moles, and preferably from 3–4 moles, for every mole of 4-halocarbonyl-piperidine utilized in the reaction.

It is preferred that the Friedel-Crafts acylation be conducted for a period of time ranging from 0.2 to 24 hours.

It is also preferred that the Friedel-Crafts acylation be conducted at a temperature range of from 0°–100° C. The reaction can either be conducted neat or in an organic solvent.

The desired 4-substituted-piperidinyl intermediate can be recovered from the reaction zone by techniques known in the art. If the phenyl ring of the 4-substituted piperidinyl intermediate is substituted with either an amino grouping or an amide grouping (i.e., Y in Formula I is H or $CO(CH_2)_nCH_3$); then the intermediate can be recovered from the reaction zone by extraction with an organic solvent, after water has been added to the reaction and the reaction zone has been rendered basic. The resulting extract can be further purified or utilized as in the next step of the synthesis. If the phenyl ring of the 4-substituted-piperidinyl intermediate is substituted with a sulfonamide grouping (i.e., Y in Formula I is $SO_2(CH_2)_nCH_3$), then the intermediate can be recovered by adding water to the reaction zone and recovering the resulting precipitated hydrohalide salt.

If desired, the 4-substituted piperidinyl intermediate can be purified by techniques known in the art.

The next step in the synthesis of the carbonyl containing 1,4-disubstituted piperidinyl compounds is to react the 4-substituted piperidinyl intermediate (compound of Formula IV) obtained above with a compound of the formula:

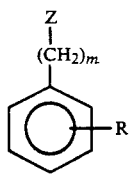

Formula V wherein R and m are as defined in Formula I and Z is selected from Br, Cl or I.

The aralkyl halide (compound of Formula V) utilized as a starting material, preferably corresponds structurally to its counterpart in the desired 1,4-disubstituted piperidinyl compound since all of its substituents with the exception of the halogen atom (Z) will be retained in the final product.

For example, if the desired 1,4-disubstituted piperidinyl compound is N-[4-[[1-(2-phenylethyl)-4-piperidinyl]carbonyl]phenyl]-acetamide, then 1-halo-2-phenyl-ethane should be utilized as the aralkyl halide reactant.

It is currently preferred that the 4-substituted piperidinyl intermediate (compound of Formula IV) and the aralkyl halide (compound of Formula V) be present in the reaction zone in approximately equimolar quantities. A slight excess of either reactant will not be deleterious to the reaction.

It is preferred that the reaction be conducted in the presence of a base. If the phenyl ring of the 4-substituted piperidinyl intermediate is substituted with a sulfonamide group (i.e., Y in Formula I is $SO_2(CH_2)_nCH_3$), then weak bases such as $KHCO_3$ are preferred. If the phenyl ring of the 4-substituted piperidinyl intermediate is substituted with either an amino grouping or an amide grouping (i.e., Y in Formula I is H or $CO(CH_3)_nCH_3$), then stronger bases such as $K_2CO_3$ or $Na_2CO_3$ may be utilized.

Preferably the base is present in the reaction zone in the molar ratio of from 1 to 2 moles of base per mole of 4-substituted piperidinyl intermediate utilized.

The reaction is currently conducted in a solvent. Representative examples of suitable solvents include N,N-dimethylformamide, toluene and the combination of toluene and water.

It is also preferred that the reaction be conducted in an inert atmosphere. Argon is currently utilized.

It is also preferred that the reaction be conducted at a temperature range of from 50°–153° C., more preferably from 90°–95° C. It is also preferred that the reaction be conducted for a period of time ranging from 0.5 to 24 hours.

It is currently preferred that the solvent be removed from the reaction zone prior to the recovery of the desired 1,4-disubstituted piperidinyl compound. This can be accomplished by filtration or other suitable techniques known in the art. The separated solvent which contains the desired product is generally concentrated prior to further purification.

The desired 1,4-disubstituted piperidinyl compound can be recovered from the concentrate by extraction with an organic solvent after water has been added to the concentrate.

The desired 1,4-disubstituted piperidinyl compound can be purified by techniques conventionally used within the art. One suitable technique is to recrystallize the 1,4-disubstituted piperidinyl compounds from an appropriate solvent system. Representative examples of suitable solvent systems include 2-propanol/hexane, ethyl acetate/methanol, and the like.

Optionally, the 1,4-disubstituted piperidinyl compound can be subjected to chromatography on a silica gel column prior to its being recrystallized.

If the desired 1,4-disubstituted piperidinyl compound is substituted with a hydroxymethyl group at the 4-position of the piperidinyl ring (i.e., X in Formula I is CHOH), then the following synthesis can be utilized.

A 1,4-disubstituted piperidinyl compound is prepared having a carbonyl function at the 4-position of the piperidinyl ring (i.e., X in Formula I is CO) that is otherwise structurally analogous to the desired hydroxymethyl containing 1,4-disubstituted piperidinyl compound. This can be accomplished in the manner disclosed above.

The carbonyl containing 1,4-disubstituted piperidinyl compound produced above can then be subjected to a reduction reaction, thereby producing the desired 1,4-disubstituted piperidinyl compound having a hydroxymethyl group located at the 4-position of the piperidinyl ring.

It is preferred that the carbonyl containing 1,4-disubstituted piperidinyl compound prepared correspond structurally to the desired hydroxymethyl containing 1,4-disubstituted piperidinyl compound since all of its other substituents will be retained in the final product.

For example, if the desired compound is N-[4-[hydroxy[1-(2-phenylethyl)-4-piperidinyl]methyl]phenyl]-acetamide; then N-[4-[[1-(2-phenylethyl)-4-piperidinyl]carbonyl]phenyl]acetamide should be prepared in the manner previously disclosed and then reduced with an appropriate reducing agent thereby producing the desired compound.

A variety of reducing agents can be utilized to reduce the carbonyl function into an alcohol. Representative examples of suitable reducing agents can be selected from the group consisting of sodium borohydride, lithium borohydride, aluminum isopropoxide, platinum metal catalyzed hydrogenations, etc.

It is preferred that the reducing agent be present in the reaction zone in a slight to moderate molar excess relative to the carbonyl containing 1,4-disubstituted piperidinyl compound.

It is preferred that the reducing agent and the 4-carbonyl substituted piperidinyl compound be allowed to react for a period of time ranging from 0.1 to 16 hours and at a temperature range of from 0°–20° C.

It is also preferred that the reaction be conducted in a solvent. Representative examples of suitable solvents include methanol, ethanol, isopropanol and dioxane.

The desired hydroxymethyl containing 1,4-disubstituted piperidinyl compound can be recovered from the reaction zone in the manner previously disclosed for the carbonyl containing 1,4-disubstituted piperidinyl compounds. Prior to further purification, it is preferred that the resulting extract be subjected to chromatographic purification technique such as flash chromatography.

If the desired hydroxymethyl containing 1,4-disubstituted piperidinyl compound is present as a free base, it can be purified by consecutive recrystallizations from differing solvent systems. One suitable combination is recrystallization from dichloro-methane/hexane, followed by isopropanol/water. An alternative is recrystallization from 2-propanol/hexane followed by recrystallization from 2-propanol. If the desired hydroxymethyl containing 1,4-disubstituted piperidinyl compound is present as its acid addition salt, then it can be purified by recrystallization from a solvent system such as methanol/ethyl acetate or methanol/isopropanol.

An alternative method of preparing the hydroxymethyl containing 1,4-disubstituted piperidinyl compounds (i.e., where X in Formula I is CHOH), is the following synthetic procedure.

The first step in the synthesis is to prepare a 4-substituted piperidinyl intermediate as previously described in Formula IV. This intermediate should be structurally analogous to the 4-substituted piperidinyl residue appearing in the final product, with the exception of X being represented by a carbonyl group. The intermediate of Formula IV is then subjected to a reduction reaction, thereby converting the carbonyl substituent at the 4-position of the piperidinyl ring into a hydroxymethyl group. This reduction reaction can be conducted in an analogous manner to the reduction previously described.

The reduced intermediate is then reacted with an aralkyl halide as previously described in Formula V, in a manner analogous to that previously described, thereby producing the desired hydroxymethyl containing 1,4-disubstituted piperidinyl compound.

For example, if the desired hydroxymethyl containing 1,4-disubstituted piperidinyl compound is N-[4-[hydroxy-[1-(2-phenylethyl)-4-piperidinyl]methyl]phenyl]-acetamide, then the first step is to prepare the intermediate of Formula IV, N-[4-(4-piperidinyl-carbonyl)-phenyl]-acetamide. This intermediate is then reduced, thereby producing N-[4-(4-piperidinylhydroxymethyl)-phenyl]-acetamide.

This reduced intermediate is then reacted with 1-halo-2-phenylethane, thereby producing N-[4-[hydroxy-[1-(2-phenylethyl)-4-piperidinyl]methyl]phenyl]-acetamide.

If the desired 1,4-disubstituted piperidinyl compound is substituted with an oxime group at the 4-position of the piperidinyl ring (i.e., X in Formula I is C=N—O—A), then the following synthesis can be utilized.

A 1,4-disubstituted piperidinyl compound is prepared having a carbonyl function at the 4-position of the piperidinyl ring (i.e., X in Formula I is CO) that is otherwise structurally analogous to the desired oxime containing 1,4-disubstituted piperidinyl compound. This can be accomplished in the manner disclosed above.

The carbonyl containing 1,4-disubstituted piperidinyl compound can then contacted with a hydroxylamine or an alkoxyamine, and via a nucleophilic addition reaction, the desired piperidinyl compound having an oxime at the 4-position of the piperidinyl ring will be produced.

The hydroxylamine or alkoxyamine which is utilized in the reaction can be described by the following formula:

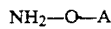

Formula VI wherein A is represented by hydrogen or a $C_{1-4}$ alkyl. In the amine which is utilized, A should be analogous to that appearing in the desired product. It also is preferred that the carbonyl containing 1,4-disubstituted piperidinyl compound utilized in the nucleophilic addition, correspond structurally to the desired oxime containing 1,4-disubstituted piperidinyl compound since all of its other substituents will be retained in the final product.

For example if the desired oxime containing compound is N-[4-[(methoxyimino)[1-(2-phenylethyl)-4-piperidinyl]methyl]phenyl-methanesulfonamide, then the appropriate reactants are N-[4-[[1-(2-phenylethyl)-4-piperidinyl]-carbonyl]phenyl]-methanesulfonamide and methoxyamine.

The nucleophilic addition is accomplished according to techniques known in the art. The carbonyl containing 1,4-disubstituted piperidinyl compound is contacted with the hydroxyl or alkoxy amine in the presence of a weak organic base such as, for example, ammonium acetate. The reactants are typically stirred together for a period of time ranging from 0.5 hours to 5 hours at a temperature range of from 0 to 120° C. It is preferred that the carbonyl containing 1,4-disubstituted piperidinyl compound and the hydroxyl or alkoxy amine be present in an approximately equimolar quantity.

The desired oxime can be recovered from the reaction zone according to techniques known in the art. Typically the reaction zone will be contacted with a base such as sodium bicarbonate and the resulting aqueous layer is then extracted with an organic solvent such as ethyl acetate. The desired oxime will be located in the resulting organic layer. The acid addition salt of the oxime product can be formed as known in the art, and is typically done prior to purification.

The oxime can also be purified according to techniques known in the art. For example if the product is present as the hydrochloride salt, it can be purified by recrystallization from a methanol/2-butanone solvent system. Other solvent systems suitable for use with other acid addition salts of the oxime product will be readily apparent to those skilled in the art.

Although those compounds of Formula I wherein Y is represented by hydrogen can be prepared utilizing the above described techniques, the synthetic procedure described below is currently utilized for their production.

Initially a 1,4-disubstituted piperidinyl compound as described by Formula I is prepared that is structurally analogous to the desired compound with the exception of Y be represented by $CO(CH_2)_nCH_3$ (i.e. an acetamide derivative). This can be done by the methods discussed above.

This 1,4-disubstituted piperidinyl acetamide derivative is then subjected to a hydrolysis reaction which serves to remove the acetyl residue and produces the desired compound wherein Y is H. Either an acidic or a basic hydrolysis can be utilized according to techniques known in the art. If X is represented by CHOH, then a basic hydrolysis should be utilized.

For example, the acidic hydrolysis can be conducted by contacting the acetamide derivative with a mineral acid such as hydrochloric acid. Typically the mineral acid is present in a concentration of from 0.5 to 12 moles per liter. The acetamide derivative is stirred in the acidic environment for a period of time ranging from 0.5 to 12 hours at a temperature range of from room temperature to 100° C.

The desired amino-substituted compound (i.e. Y is H) can be recovered using techniques known in the art. Typically the reaction medium is neutralized with a base when an acidic hydrolysis is utilized and then extracted with an organic solvent such as chloroform.

The amino compound can also be purified using techniques known in the art. The organic layer obtained above is concentrated and dried. The concentrate is then filtered thru silica gel by eluting with acetone. The eluent is then concentrated until a solid is obtained. This solid is then subjected to recrystallization in a solvent such as isopropanol. Other solvent systems will be readily apparent to those skilled in the art.

The compounds of Formula I can be administered by a variety of routes. They are effective if administered either orally or parenterally (i.e., intravenously, intramuscularly, or subcutaneously).

Repetitive daily administration of the compounds may be desired and will vary with the conditions outlined below for the quantity of compound utilized.

The compounds of the present invention are useful as cardiac antiarrhythmic agents. They can be administered to a patient suffering from an arrhythmic episode in order to terminate the arrhythmic episode and return the myocardium to a normal sinus rhythm or the compound can be administered on a prophylactic basis in order to prevent the occurrence of arrhythmic episodes.

The compounds of Formula I increase the duration of the action potential of myocardial tissue producing an increase in the refractory period of that tissue. Thus, under the classification system of Vaughan Williams these compounds exhibit a Class III antiarrhythmic activity.

One method of demonstrating the antiarrhythmic activity of these compounds is the following test protocol. This protocol demonstrates what effect a compound has upon the action potential of isolated card.:ac tissue, such as a Purkinje fiber from a dog heart or a papillary muscle from a guinea pig heart.

The heart of an anesthetized mongrel dog is surgically removed and the Purkinje fibers are dissected from either of the ventricles. Alternatively, papillary muscles are removed from the right cardiac ventricle of a guinea pig. A Purkinje fiber or a papillary muscle is then placed in a tissue bath which is continuously perfused with modified Tyrode's solution[1].

[1] The modified Tyrode's solution has the following composition (in mMol): NaCl 127.0, KCl 5.4, NaH$_2$PO$_4$ 0.5, MgCl$_2$ 1.0, NaHCO$_3$ 23.8, CaCl$_2$ 1.8 and glucose 11.1. A gas mixture comprised of 95% O$_2$ and 5% CO$_2$ is bubbled through the solution while it is maintained within a pH range of from 7.3–7.4.

The electrophysiology of the cardiac tissue is monitored by conventional glass microelectrodes. One microelectrode is inserted into a cell in the cardiac muscle fiber and a ground electrode is positioned in the tissue bath. A conventional oscilloscope is utilized to visualize the action potential waveforms of the cardiac cell.

The cardiac muscle fiber is electrically stimulated at a frequency of 1 Hz through a pair of platinum plates placed in the tissue bath. This stimulation is continued for approximately 1 hour in order to allow the electrophysiological characteristics of the fiber to stabilize.

After approximately 1 hour, the fiber should be exhibiting a stable action potential as demonstrated by the waveform displayed on the oscilloscope. At this point, representative control action potentials are recorded and analyzed by a computer.

After establishing a control action potential, the test compound is introduced into the Modified Tyrode's solution in a quantity such that the test compound is present within the tissue bath in a range of from $10^{-8}$ to $10^{-5}$ moles/liter. After the effect of the test compound has reached a steady state, the action potential is again recorded and analyzed in the manner described above.

The compounds of the present invention having Class III antiarrhythmic properties are useful for treating a variety of arrhythmic conditions of the heart. Representative examples of arrhythmic conditions which are amendable to treatment with the compounds of the present invention include atrial tachycardia, atrial flutter, atrial fibrillation, supra ventricular arrhythmias, and life threatening ventricular arrhythmias such as ventricular tachycardia, or ventricular fibrillation. These compounds will also prevent recurrent episodes of the arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, the presence of other underlying disease states, and the particular compound utilized. However as a general guideline, if the compound is being administered orally, then it is preferably administered within a dosage range of from about 1.0 to about 400.0 mg/kg of patient body weight/day. Likewise, if the compound is being administered parenterally then it is preferably administered within a dosage range of from about 0.1 to about 120 mg/kg of patient body weight/day.

The patient's response to the compound can be monitored via an EKG or any other technique conventionally used in the art.

In addition to exhibiting an antiarrhythmic effect upon cardiac tissue at the doses described above, those compounds of Formula I wherein Y is represented by SO$_2$(CH$_2$)$_n$CH$_3$ and X is represented by CO increase the contractile force of cardiac tissue, (i.e. a cardiotonic effect). This can be demonstrated in vitro by measuring the force of contraction in guinea pig papillary muscle.

Additionally the following known antiarrhythmic compounds increase the contractile force of cardiac tissue within the dosage ranges described above:

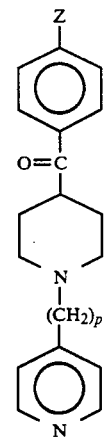

wherein p is an integer from 1–6 and Z is represented by NHSO$_2$R$^1$; in which R$^1$ is C$_{1-6}$ alkyl. These compounds, their acid addition salts, their optical isomers, as well as methods for their production are known in the art. European Patent Application C235,752 discloses this.

The compounds of Formula I are also non-narcotic analgesic agents. The compounds possess a level of potency sufficient to inhibit the sensation of the severe levels of pain that are commonly associated with conditions such asmetastatic carcinoma, myocardial infarctions or traumatic injuries.

Despite this high level of potency, the compounds are non-narcotic. This means that they are devoid of the abuse potential that accompanies most analgesics.

One manner of demonstrating the analgesic utility of these compounds is to conduct the following test protocol. From 5 to 10 mice, should be administered from 0.1 to 200 mg/kg of the compound either subcutaneously or intragastrically. Thirty minutes after the administration of the test compound, the mice should be administered 0.4 ml of a 0.25% v/v solution of acetic acid intraperitoneally.

Five minutes after the administration of the acetic acid, the mice should be observed for signs of squirming and writhing which is indicative of pain.

A compound is considered to posses significant analgesic activity if the mice which are administered said compound do not exhibit signs of pain during the test (i.e., squirming and writhing).

One manner of demonstrating the non-narcotic properties of these compounds is the following test protocol.

Three mice should be administered up to 800 mg/kg of the desired compound intraperitoneally. Thirty minutes later the mice should be placed upon a hot plate which has been heated to a temperature of 55° C.

A compound is considered to be non-narcotic if the mice jump within the first 20 seconds of when they are initially placed upon the hot plate.

The quantity of compound required to produce this analgesic effect can vary widely depending upon the particular compounds utilized, the severity of the patient's pain, the patient, the presence of other underlying disease states, the route of administration, and other therapeutic agents which are being administered to the patient. Generally though, the compounds will produce an analgesic effect at a dosage range of from about 0.5 mg/kg of patient body weight/day to about 100 mg/kg of patient body weight/day if administered parenterally and from about 2 mg/kg of patient body weight/day to about 200 mg/kg of patient body weight/day if administered orally.

The compounds of Formula I are also serotonin $5HT_2$ antagonists. The ability of the compounds to antagonize the effects of serotonin at the $5HT_2$ receptor can be demonstrated by the following protocol. In this test, 5HT2 receptors are exposed to both [$^3$H] spiroperidol, (a substance known to have a non-specific affinity for the receptor) and the test compound. The extent to which there is a decrease in binding of the [$^3$H] spiroperidol to the receptor is indicative of the affinity of the test compound for the $5HT_2$ receptor.

Initially a suspension of $5HT_2$ receptors should be prepared. Rat cerebrocortex tissue is homogenized in 30 volumes of ice cold 50 mM Tris Cl buffer, pH 7.7, using a polytron (setting 7 for 10 seconds). The homogenate is centrifuged at 40,000 X g for 10 minutes at 4° C. The pellet is resuspended in 30 volumes of ice-cold buffer using a Dounce homogenizer and centrifuged as before. The pellet is finally resuspended in 30 volumes of buffer.

To incubation tubes are added 0.2 ml of the receptor suspension, 100 µl of a 0.6 nM solution of [$^3$H] spiroperidol, 100 µl of a solution containing the test compound (present within a concentration range of from $10^{-5}$ to $10^{-10}$ moles per liter) and enough buffer to produce a final volume of 1.0 ml. The tubes are then incubated at 37° C. for 15 minutes. The incubation is quickly terminated by adding 5 ml of ice-cold buffer to the test tubes and filtering the cooled suspension through a glass fiber filter under vacuum.

The filters are washed twice with 5 ml of cold buffer and then the filters are transferred scintillation vials. The filters are then analyzed via liquid scintillation spectrometry in 8.0 ml of Omnifluor ® containing 5% Protosol ®.

The specific binding of [$^3$H] spiroperidol is measured as the excess over blanks made with 10 µM methiothepin. A test compound is considered to have affinity for the $5HT_2$ receptor if it displaces the [$^3$H] spiroperidol by a factor of at least 15%.

The ability of the compounds to antagonize the $5HT_2$ receptor in vivo can be demonstrated via the following test protocol.

At least 5 mice should be administered from 0.1 mg/kg to 200 mg/kg of the test compound. Approximately 30 minutes later, the animal is administered 30 mg/kg of 5-methoxy-N,N-dimethyltryptamine (DMT) intraperitoneally. For six minutes immediately following the administration of the DMT, the number of head twitches for each animal is counted. An absence of head twitches, is considered indicative of the ability of the compound to antagonize the $5HT_2$ receptor in vivo.

The dosage range at which these compounds exhibit their ability to block the effects of serotonin at the $5HT_2$ receptor can vary depending upon the particular compound being administered, the particular disease or condition being treated and its severity, the patient, other underlying disease states the patient is suffering from, and other medications that may be concurrently administered to the patient. Generally though, these compounds will exhibit their serotonin $5HT_2$ antagonist properties at a dosage range of from about 0.2 mg/kg of patient body weight/day to about 100 mg/kg of patient body weight/day.

Since the compounds are serotonin $5HT_2$ antagonists, they are useful in the treatment of a variety of disease states and conditions. The compounds of Formula I are useful in the treatment of anxiety, variant angina, anorexia nervosa, Raynaud's phenomenon, intermittent claudication and coronary or peripheral vasospasms. These conditions and diseases can be relieved by administering to a patient in need thereof of, a compound of Formula I in an amount sufficient to treat the disease or condition (i.e. an anxiolytic amount, anti-anginal amount, anti-anorexic amount, etc.). This quantity will be within the dosage range at which the compounds exhibit their serotonin $5HT_2$ antagonistic properties.

The compounds are also useful in the treatment of thrombolytic illnesses. As known to those skilled in the art, a variety of conditions can cause the initial aggregation of platelets. This initial aggregation of platelets produces a release of serotonin which induces the further aggregation of platelets. This further aggregation also stimulates the further release of serotonin. Thus a cycle is created wherein the clot can expand until the blood vessel is occluded. It has been discovered that the compounds of Formula I prevent the further aggregation of platelets which is typically produced as the result of the release of serotonin. Thus the compounds can be administered prophylactically in an anti-thrombotic quantity to a patient in need thereof to prevent the formation of thrombi capable of occluding blood vessels. This anti-thrombotic amount will be within the dosage range described above wherein these compounds exhibit their serotonin $5HT_2$ antagonist effects. Representative examples of patients who can benefit from such therapy include patients with atherosclerosis and coronary artery disease that are experiencing transient ischemic attacks characterized by chest pains (angina pectoris) or other usual symptoms and patients who are undergoing thrombolysis with agents such as streptokinase or tissue plasminogen activator as well as patients undergoing coronary bypass surgery.

The compounds of Formula I are also useful in the treatment of fibromyalgia. As used in this application, fibromyalgia refers to a chronic disease state wherein the patient suffers from numerous symptoms such as for example, widespread generalized musculoskeletal pains, aching, fatigue, morning stiffness and a sleep disturbance which can be characterized as an inadequacy of stage 4 sleep. Administration of the compounds of Formula I in a antifibromyalgia amount relieves or alleviates the symptoms the patient is experiencing. An antifibromyalgia amount will be within the dosage range described above wherein these compounds exhibit their serotonin $5HT_2$ antagonist effects.

The compounds of Formula I can also be used to treat the extrapyramidal symptoms that often accompany the administration of neuroleptic agents such as haloperidol, chlorpromazine, etc. These extrapyramidal side effects (EPS) can manifest themselves in a variety of ways. Some patients experience a parkinsonian-like syndrome, wherein they experience muscular rigidity and tremors. Others experience akathisia, which can be characterized as a compelling need for the patient to be in constant movement. A few patients experience acute dystonic reactions, such as facial grimacing and torticollis.

The administration of a compound of Formula I to a patient in need thereof, in an anti-EPS amount will relieve or alleviate the symptoms that the patient is experiencing. The amount of compound which produces this anti-EPS effect is an amount within the dosage range at which the compounds exhibit their serotonin $5HT_2$ antagonistic effects.

As used in this application:

a) the terms anxiety, variant angina, anorexia nervosa, Raynaud's phenomenon, and coronary vasospasms are used in the manner defined in the 27th Edition of Dorland's Illustrated Medical Dictionary, b) the term patient refers to a warm-blooded animal, such as for example rats, mice, dogs, cats, guinea pigs, and primates such as humans.

c) the term arrhythmia refers to any variation from the normal rhythm of the heart beat. Also as used in this application, the term antiarrhythmic refers to a compound capable of either preventing or alleviating an arrhythmia, d) the term analgesic refers to an agent which either relieves or alleviates the sensation of pain, e) the term thrombolytic illness refers to the formation of thrombi capable of occluding blood vessels, f) the term treat refers to either relieving or alleviating the patient's disease or condition and, g) the phrase "increasing the contractile force of cardiac tissue" refers the ability of the compounds to increase the strength of the muscular contractions occurring within the cardiac tissue.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The following examples are presented in order to further illustrate the present invention. However, they should not be construed as limiting the scope of the invention in any manner.

EXAMPLE 1

The purpose of this example is to demonstrate a manner of preparing an intermediate of Formula IV, N-[4-(4-piperidinyl-carbonyl)phenyl]-acetamide.

33.9 g of N-phenyl-acetamide (251 mmol) was admixed with 45 g of $AlCl_3$ (338 mmol). This mixture was placed in a 5 liter round bottom flask, mechanically stirred and heated with steam until a dark viscous solution was obtained.

To this solution was added consecutively 46.0% of 4-chloro-carbonyl piperidine hydrochloride (250 mmol) and 90 g of $AlCl_3$ (675 mmol). This produced a dark red paste.

The paste was heated with steam for 15 minutes and then 100 ml of 1,1,2,2-tetrachloroethane was added which produced a translucent red solution. This solution was then heated for an additional 10 minutes.

The steam bath was then removed and the reaction was quenched by the slow addition of 2 kg of cracked ice. The solution was made strongly basic with a 50% NaOH solution. This cold aqueous solution was then washed twice with toluene, and extracted twice with chloroform. The combined chloroform extracts were dried over $MgSO_4$ and evaporated to yield a yellow solid. The solid was washed in refluxing ethyl acetate at 76° C and filtered to afford N-[4-(4-piperidinyl-carbonyl)phenyl]-acetamide (20 g) as a light yellow solid.

A portion of this product was then converted into a hydrochloride acid addition salt in the following manner.

To 30 ml of stirred methanol under argon at 0° C. was added acetyl chloride (0.95 ml, 0.86 g, 13.4 mmol) dropwise with a syringe. This solution was then added dropwise to 3.0 g of the N-[4-(4-piperidinyl-carbonyl)-phenyl]-acetamide (12.2 mmol, prepared above) which had been dissolved in 50 ml of methanol.

This solution was then heated to reflux and diluted with 100 ml of refluxing ethanol. This admixture was then concentrated to a volume of 75 ml.

The solution was cooled to room temperature which caused the precipitation of the intermediate N-[4-(4-piperidinyl-carbonyl)phenyl]-acetamide as the monohydro-chloride salt. 1.7 g of N-[4-(4-piperidinyl-carbonyl)-phenyl]-acetamide monohydrochloride (6.0 mmol) was obtained which had a melting point of 285° C.

EXAMPLE 2

The purpose of this example is to demonstrate a manner of preparing the 1,4-disubstituted piperidinyl compound, N-[4-[[1-(2-phenylethyl)-4-piperidinyl]carbonyl]phenyl]-acetamide.

13.0 g of N-[4-(4-piperidinyl-carbonyl)phenyl]-acetamide (52.8 mmol) was prepared in the manner disclosed in Example 1 and admixed with 9.62 g of 1-bromo-2-phenylethane (52.0 mmol), 13.0 g of $K_2CO_3$ (94.1 mmol) and 150 ml of N,N-dimethylformamide. This admixture was stirred under an argon atmosphere at 95° C. for 16 hours.

The mixture was then cooled to 22° C and the N,N-dimethylformamide was removed from the salts by decantation. The decanted N,N-dimethylformamide was concentrated at reduced pressure on a rotary evaporator until a tan solid was obtained.

This tan solid was partitioned between water and dichloromethane. The layers were separated and the organic layer was saved for further recovery. The aqueous layer was extracted with dichloromethane and the resulting organic layer was saved for further purification.

The two previously saved organic layers were then dried over $MgSO_4$ and evaporated on a rotary evaporator until a yellow oil was obtained.

The yellow oil was then dissolved in 150 ml of 2-propanol which had been heated to reflux. This solution was then diluted with refluxing hexane until a total volume of 500 ml had been obtained.

The solution was then cooled to approximately 22° C. and filtered. 1.3 g of N-[4-[[1-(2-phenylethyl)-4-piperidinyl]carbonyl]phenyl]-acetamide (40.8 mmol) was obtained.

A portion of this product was then converted into a hydrochloride acid addition salt in the following manner.

To 30 ml of stirred methanol which had been cooled to 0° C. was added acetyl chloride (0.9 ml, 0.99 g, 12.6 mmol) dropwise via a syringe under an argon atmosphere.

4.0 g of the N-[4-[[1-(2-phenylethyl)-4-piperidinyl]carbonyl]phenyl]-acetamide (8.3 mmol, prepared above) was dissolved in 600 ml of methanol. To this solution was added dropwise the solution of HCl in methylacetate/methanol described above.

After completion of the addition, the solution was stirred for 5 minutes and then concentrated by a rotary evaporator at a reduced pressure to a final volume of 80 ml.

Ethyl acetate was then slowly added to the solution which caused the precipitation of crude N-[4-[[1-(2-phenylethyl)-4-piperidinyl]carbonyl]phenyl]-acetamide monohydrochloride.

The precipitate was then dissolved in refluxing methanol and admixed with activated charcoal, and filtered. The filtrate was admixed with 2-propanol which had been heated to a temperature of 82° C. and the desired compound crystallized after cooling.

The product was filtered and dried to give 2.6 g of N-[4-[[1-(2-phenylethyl)-4-piperidinyl]carbonyl]phenyl]-acetamide hydrochloride, m.p. 257° C.

EXAMPLE 3

The purpose of this example is to demonstrate a manner of preparing an intermediate of Formula IV, N-[4-(4-piperidinyl-carbonyl)phenyl]-methanesulfonamide monohydrochloride.

42.8 g of N-phenyl methanesulfonamide (250 mmol) was admixed with 45 g of $AlCl_3$ (338 mmol) in a 5 liter round bottom flask and heated with steam while being mechanically stirred. A dark viscous solution was obtained.

This solution was mixed with 46.0 g of 4-chlorocarbonyl piperidine hydrochloride (250 mmol) and 90.0 g of $AlCl_3$ (675 mmol) which produced a dark brown sludge.

1,1,2,2-Tetrachloroethane (100 ml) was added and the admixture was heated for an additional 15 minutes.

Heating was discontinued and the reaction was quenched by the addition of 4 kg of cracked ice. A gray precipitate was obtained.

The precipitate was recovered by filtration. The resulting solid was washed consecutively with water and ethyl ether and then air dried.

The resulting solid was dissolved in hot water, admixed with activated charcoal and filtered. The solution was then cooled to approximately 22° C. at which point the desired product precipitated from solution.

The solid material was filtered and dried to give 29.6 g of N-[4-(4-piperidinyl-carbonyl)phenyl]-methanesulfonamide monohydrochloride (92.8 mmol) which had a melting point of 303°-305° C.

EXAMPLE 4

The purpose of this example is to demonstrate a manner for preparing the 1,4-disubstituted piperidinyl compound, N-[4-[[1-(2-phenylethyl)-4-piperidinyl]-carbonyl]phenyl]-methanesulfonamide.

11.1 g of N-[4-(4-piperidinyl-carbonyl)phenyl]-methane-sulfonamide monohydrochloride (34.8 mmol) prepared as in the manner disclosed in Example 3 was admixed with 6.5 g of 1-bromo-2-phenylethane (35.2 mmol) and 7.1 g of $KHCO_3$ (71.0 mmol) and 100 ml of N,N-dimethylformamide.

This admixture stirred under an argon atmosphere for 16 hours at a temperature of 90° C.

This admixture was then cooled to approximately 22° C. The N,N-dimethylformamide was decanted off and was concentrated on a rotary evaporator, thereby producing a tan solid.

This solid was partitioned between water and dichloromethane. The layers were separated and the organic layer was saved for further purification. The aqueous layer was extracted with dichloromethane and the organic layer was separated and saved for further purification.

The organic layers were combined, dried over $MgSO_4$ and then concentrated at reduced pressure on a rotary evaporator which produced a yellow oil.

The oil was then dissolved in acetone and filtered through a pad of silica gel. The resulting filtrate was then concentrated to an oil which was diluted with 2-butanone which had been heated to reflux.

The butanone solution was cooled to approximately 22° C. and filtered thereby producing yellow crystals which were air dried.

3.2 g of N-[4-[[1-(2-phenylethyl)-4-piperidinyl]-carbonyl]phenyl]-methanesulfonamide (8.3 mmol) was obtained.

Methanol (1.5 ml) was admixed with 25 ml of ethyl acetate and cooled to 0° C. To this solution was added acetyl chloride (0.73 ml, 0.66 g, 8.5 mmol) dropwise with a syringe under an argon atmosphere.

After 5 minutes, this solution was added to the 3.2 g of N-[4-[[1-(2-phenylethyl)-4-piperidinyl]carbonyl]phenyl]-methanesulfonamide (8.3 mmol, prepared above) which had been dissolved in 200 ml of stirred ethyl acetate.

This addition caused the precipitation of a white solid. The solid was recovered from the solution by filtration and air dried.

The solid was then dissolved in approximately 100 ml of refluxing methanol, admixed with activated charcoal and filtered. The filtrate was admixed with 2-propanol and the desired compound was obtained by recrystallization.

2.0 g of N-[4-[[1-(2-phenylethyl)-4-piperidinyl]-carbonyl]phenyl]-methanesulfonamide monohydrochloride (4.7 mmol) was obtained which had a melting point of 117.5°-118.5° C.

EXAMPLE 5

The purpose of this example is to demonstrate a manner of preparing the hydroxymethyl containing 1,4-disubstituted piperidinyl compound, N-[4-[hydroxy-[1-(2-phenylethyl)-4-piperidinyl]methyl]phenyl]-acetamide.

5.0 g of N-[4-[[1-(2-phenylethyl)-4-piperidinyl]carbonyl]phenyl]-acetamide (prepared in the manner described in Example 2) was admixed with 250 ml of methanol, and then was cooled to 0° C. The solution was stirred while 0.54 g of sodium borohydride (14.3 mmol) was added. The solution was stirred for an additional hour.

An additional 0.5 g of sodium borohydride was added and the solution was stirred overnight.

The next morning 100 ml of water was added to the solution. The solution was then concentrated at reduced pressure to approximately ½ volume. The concentrate was subjected to two extractions with dichloromethane and the resulting organic layers were combined for further purification.

The organic layers were dried over $MgSO_4$ and filtered through a pad of silica gel utilizing an acetone eluent. The filtrate was then evaporated at reduced pressure by a rotary evaporator, thereby producing a white solid.

The desired hydroxymethyl containing 1,4-disubstituted piperidinyl compound was obtained from the white solid by: a) recrystallization from a dichloromethane/hexane solvent system, and b) subsequent recrystallization from an isopropanol/water solvent system. The resulting white needles were dried at 79° C and 0.5 mm Hg for 40 hours.

1.44 % of N-[4-[hydroxy[1-(2-phenylethyl)-4-piperidinyl]methyl]phenyl]-acetamide (3.7 mmol) was obtained which had a melting point of 173°-174° C.

EXAMPLE 6

The purpose of this example is to demonstrate a manner of preparing the hydroxymethyl containing 1,4-disubstituted piperidinyl compound, N-[4-[hydroxy-[1-(2-phenylethyl)-4-piperidinyl]methyl]phenyl]-methanesulfonamide.

4.85 g of N-[4-[[1-(2-phenylethyl)-4-piperidinyl]-carbonyl]phenyl]-methanesulfonamide hydrochloride (11.5 mmol) which had been prepared in the manner disclosed in Example 4 was admixed with 500 ml of methanol and then cooled to 0° C. The solution was stirred and 3.2 g of sodium borohydride (84.6 mmol) was added to this solution in 3 portions over the next 3 hours.

The solution was stirred overnight and concentrated at reduced pressure on a roto evaporator. The resulting white solid was partitioned between water and chloroform. The organic layer was saved for further purification. The aqueous layer was extracted with chloroform and the resulting organic layer was saved.

The organic layers were combined, dried over $MgSO_4$, and then evaporated at reduced pressure by a roto evaporator to give a white solid.

The desired hydroxymethyl containing 1,4-disubstituted piperidinyl compound was purified from the white solid by: a) recrystallization from a 2-propanol/hexane solvent system and, b) subsequent recrystallization from 2-propanol.

This produced 1.9 9 of N-[4-[hydroxy-[-1-(2-phenylethyl)-4-piperidinyl]methyl]phenyl]-methanesulfonamide (4.9 mmol) which had a melting point of 164.5°-165.5° C.

EXAMPLE 7

The purpose of this example is to demonstrate a manner of preparing N-[4-[[1-2-(4-methoxyphenyl)ethyl-4-piperidinyl]carbonyl]phenyl]-methanesulfonamide.

The intermediate N-[4-(4-piperidinyl-carbonyl)-phenyl]-methanesulfonamide was prepared in a manner analogous to Example 1.

A slurry of N-[4-(4-piperidinyl-carbonyl)phenyl]-methanesulfonamide monohydrochloride (18.4 g, 57.6 mmol), 1-bromo-2-(4-methoxyphenyl)-ethane (12.4 g, 57.6 mmol), and potassium bicarbonate (11.5 g, 115 mmol) in N,N-dimethylformamide (180 ml) was stirred under argon at 100° C for 16 hours. After cooling to room temperature, the dimethylformamide was decanted away from the salts, and the solution was concentrated at reduced pressure to a dark oil. The oil, along with the salts, was partitioned between water and ethyl acetate. The layers were separated and the aqueous layer was extracted with ethyl acetate. The combined organic layers were washed twice with water, brine, dried over $MgSO_4$, and evaporated to give an off-white solid (20.6 g). The solid was dissolved in ethyl acetate (600 ml) and treated with HCl in ethyl acetate to afford a white solid (20.2 g). The solid was recrystallized from methanol/isopropanol to yield N-[4-[[1-2-(4-methoxyphenyl)ethyl]-4-piperidinyl]carbonyl]phenyl]-methanesulfonamide monohydrochloride (16.5 g, 36.3 mmol) as white, shiny flakes; m.p. 246°-247° C.

EXAMPLE 8

The purpose of this example is to demonstrate a method for the preparation of N-[4-[[1-[2-(4-fluorophenyl)ethyl]-4-piperidinyl]carbonyl]phenyl]-methanesulfonamide.

The intermediate N-[4-(4-piperidinyl-carbonyl)-phenyl]-methanesulfonamide monohydrochloride was prepared in a manner analogous to Example 1.

A slurry of N-[4-(4-piperidinyl-carbonyl)phenyl]-methanesulfonamide monohydrochloride (12.3 g, 38.4 mmol), 1-bromo-2-(4-fluorophenyl)-ethane (7.8 g, 38.4 mmol), and potassium bicarbonate (7.7 g, 77.0 mmol) in N,N-dimethylformamide was stirred under argon at 100° C for 16 hours. After cooling to room temperature, the dimethylformamide was decanted away from the salts, and the solution was concentrated to an oil. The oil, along with the salts, was partitioned between water and chloroform. The layers were separated and the aqueous layer was extracted with chloroform. The combined organic layers were dried over MgSO4 and evaporated and evaporated to give an oil (18 g). The oil was divided into two, 9 g portions, and consecutively chromatographed on silica gel, eluding with 1:4 acetone:ethyl acetate, to give a solid (11.0 g). The solid was dissolved in methanol (200 ml) and treated with HCl in methanol. The entire solution was evaporated and the resulting off-white solid was recrystallized from methanol/isopropanol to afford N-[4-[[1-[2-(4-fluorophenyl)ethyl]-4-piperidinyl]carbonyl]phenyl]-methanesulfonamide (5.94 g) as white crystals; m.p. 230°–230.5° C.

EXAMPLE 9

The purpose of this example is to demonstrate a method for the preparation of N-[4-[hydroxy-[1-[2-(4-methoxy-phenyl)ethyl]-4-piperidinyl]methyl]phenyl]-methane-sulfonamide.

To a stirred solution of N-[4-[[1-[2-(4-methoxyphenyl)ethyl]-4-piperidinyl]carbonyl]phenyl]-methane-sulfonamide (5.50 g, 13.2 mmol which had been prepared in the manner described in Example 7), in methanol (450 ml), at 0° C., was added sodium borohydride (600 mg, 15.9 mmol) in one portion. Two additional 600 mg portions of sodium borohydride were added consecutively at 1.5 hour intervals and the solution was allowed to stir overnight. The reaction mixture was evaporated to a white solid and mixed into 200 ml of dilute aqueous HCl. The aqueous solution was neutralized with sodium bicarbonate and extracted three times with chloroform. The combined organic layers were dried over MgSO4, and evaporated to give an off-white solid (5.2 g). The solid was chromatographed on silica gel, eluding with acetone, to give N-[4l-[hydroxy-[1-[2-(4-methoxyphenyl)ethyl]-4-piperidinyl]methyl]phenyl]-methanesulfonamide (15.1 g, 12.2 mmol) as an off-white solid; m.p. 40°–48° C.

EXAMPLE 10

The purpose of this example is to demonstrate a method for the preparation of N-[4-[hydroxy-[1[2-(4-fluoro-phenyl)ethyl]-4-piperidinyl]methyl]phenyl]-methane-sulfonamide.

To a stirred solution of N-[4-[[1-[2-(4-fluorophenyl)ethyl]-4-piperidinyl]carbonyl]phenyl]-methanesulfonamide (9.50 g, 23.5 mmol which had been prepared in the manner disclosed in Example 8), in methanol (500 ml), at 0° C., was added sodium borohydride (1 g, 26.5 mmol) in one portion. Three more 1-gram portions of sodium borohydride were added consecutively at 11-hour intervals and the solution was allowed to stir overnight. The solution was evaporated to dryness and the solid was stirred into dilute aqueous HCl (200 ml). The aqueous solution was neutralized with sodium bicarbonate and extracted three times with chloroform. The combined organic layers were dried over MgSO4, and evaporated to give a white solid (8.2 g). The solid was recrystallized from chloroform to afford white flakes (5.7 g). The white flakes were found to be N-[4-[hydroxy-[1l-[2l-(4-fluorophenyl)ethyl]-4-piperidinyl]methyl]phenyl]-methanesulfonamide containing one equivalent of chloroform.

EXAMPLE 11

The purpose of this example is to demonstrate a manner, of preparing N-[4l-[[1-[2-(3,4-methylenedioxyphenyl)-ethyl]-4-piperidinyl]carbonyl]phenyl]-methanesulfonamide monohydrochloride. A slurry of N-[4-(4-piperidinylcarbonyl)phenyl]-methanesulfonamide monohydrochloride (20.9 g, 65.6 mmol), 1l-bromo-2-(3,4-methylenedioxyphenyl)-ethane (15.0 g, 65.5 mmol), potassium bicarbonate (13.1 g, 131 mmol) and N,N-dimethyl-formamide (200 ml) was stirred under argon at 95° C. for 16 hours. After cooling to room temperature, the solution was filtered and the filtrate concentrated to a yellow oil. The oil was partitioned between water and ethyl acetate, the layers separated, and the aqueous layer extracted with ethyl acetate. The combined organic layers were washed with water, brine, dried (MgSO4), concentrated to ca. 100 ml, and chromatographed on silica(100×165 mm) eluting with ethylacetate. The appropriate fractions were combined and treated with hydrogen chloride to afford the product (22.0 g, 47.1 mmol,) as a white solid. The solid was refluxed in methanol and filtered to give the desired product (15.0 g, 28.0 mmol); m.p. 236°–237° C.

EXAMPLE 12

The purpose of this example is to demonstrate a manner of preparing N-[4-[hydroxy-[1-[2-(3,4-methylenedioxy-phenyl)ethyl]-4-piperidinyl]methyl]phenyl]-methane-sulfonamide.

A slurry of N-[4-[[1-[2-(3,4-methylenedioxyphenyl)ethyl-4-piperidinyl]carbonyl]phenyl]-methanesulfonamide monohydrochloride prepared as in Example 11 (10.2 g, 21.8 mmol) and methanol (400 ml) was treated with potassium borohydride (9.6, 178 mmol) in eight portions over a period of three days. The solution was acidified with 10% hydrochloric acid, and the pH adjusted to eight with saturated sodium bicarbonate. This aqueous solution was concentrated and then extracted twice with ethylacetate. The combined organic layers were dried (MgSO4), and evaporated to give a white solid (7.9 g). The solid was chromatographed on silica (75×160 mm), eluting with acetone to afford the desired product (4.8 g, 11.1 mmol) as a white solid; m.p. 72°–73° C.

EXAMPLE 13

The purpose of this example is to demonstrate a manner of preparing N-[4-[(methoxyimino)[1-(2-phenylethyl)-4-piperidinyl]methyl]phenyl-methanesulfonamide.

A solution of N-[4-[[1-(2-phenylethyl)-4-piperidinyl]-carbonyl]phenyl]-methanesulfonamide monohydrochloride prepared as in Example 4 (6.0 g, 14.2 mmol), methoxyamine monohydrochloride (3.0 g, 35.9 mmol), and ammoniumacetate (120 g, 156 mmol), was prepared in ethanol (90 ml) and water (30 ml) and refluxed for 16 hours. The solution was cooled, concentrated, and treated with aqueous sodium bicarbonate. This basic, aqueous layer was extracted twice with ethyl acetate The combined organic layers were dried (MgSO4), filtered, and treated with hydrogen chloride to afford a white solid (6 g). The solid was recrystallized from methanol/2-butanone to yield the desired product (2.3 g, 10.8 mmol) as a white, crystalline material; m.p. 234.0°–234.5° C.

EXAMPLE 14

The purpose of this Example is to demonstrate the production of a 1,4-disubstituted piperidinyl compound according to Formula I wherein Y is represented by H.

A solution of N-[4-[[1-(2-phenylethyl)-4-piperidinyl]-carbonyl]phenyl/acetamide (32.1 g, 91.6 mmol), conc hydrochloric acid (300 ml), and ethanol (300 ml) was prepared and refluxed for six hours. The cooled solution was treated with 50% NaOH (200 g), concentrated, and extracted twice with chloroform. The combined organic layers were dried (MgSO$_4$), concentrated, and filtered through a pad of silica gel (eluting with acetone). The eluent was concentrated and the resulting solid was recrystallized from isopropanol to give 4-aminophenyl 1-(2-phenylethyl)-4-piperidinyl]methanone as tan spears (20.3 g, 72%): m.p. 171°-172° C.

EXAMPLE 15

This example demonstrates a less preferred technique for the production of a piperidinyl compound according to formula I wherein Y is represented by H and X is represented by CHOH. The carbonyl group of the starting material was reduced and the acetamide group was allowed to hydrolyze in situ, rather than conducting the reduction and hydrolysis as distinct steps.

To N-[4-[[1-(2-phenylethyl)-4-piperidinyl]carbonyl]-phenyl]acetamide (40.0 g, 114 mmol) in methanol (900 ml) was added potassium borohydride (16 g, 300 mmol), in small portions, over a 6 hour period. Water (200 ml) was added and the solution was stirred for 20 hours. The solution was concentrated and partitioned between water and dichloromethane. The layers were separated, the organic layer dried (MgSO$_4$), filtered, and concentrated. The resulting material was chromatographed on silica gel, eluting with 10% methanol in chloroform. The appropriate fractions were combined, evaporated, and the resulting solid recrystallized from 2-propranol/water to afford α-(4-aminophenyl)-1-(2-phenylethyl)-4-piperidine methanol as a white solid (7.5 g, 21%): m.p. 129°-130° C.

What is claimed is:

1. A method for the treatment of thrombolytic illness comprising administering to a patient in need thereof an anti-thrombotic amount of a compound of the formula:

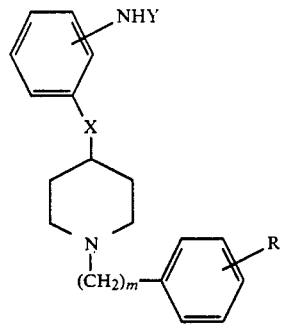

in which Y is represented by —CO(CH$_2$l)$_n$CH$_3$ n is an integer from 0-3; X is represented CO, CHOH, or C=N—O—A, wherein A is represented by hydrogen or a C$_{1-4}$ alkyl; R is either selected from the group consisting of halogens, lower alkyl groups, lower alkoxy groups, and hydrogen or R is a divalent substituent and is represented by a 3,4-methylenedioxy or a 3,4-ethylenedioxy substituent; m is an integer from 1-5; and the pharmaceutically acceptable acid addition salts thereof.

2. A method according to claim 1 wherein X is CHOH.

3. A method according to claim 1 wherein X is CO.

4. A method according to claim 1 wherein X is C=NOA.

5. A method according to claim 1 wherein said compound is N-[4[hydroxy[1-(2-phenylethyl)-4-piperidinyl]methyl]phenyl]-acetamide.

6. A method according to claim 1 wherein said compound is N-[4-[hydroxy[1-[2-phenylethyl)-4-piperidinyl]methyl]phenyl]acetamide.

* * * * *

UNITED STATES PATENT AND TRADEMARK OFFICE
CERTIFICATE OF CORRECTION

PATENT NO.  : 5,093,341
DATED       : March 3, 1992
INVENTOR(S) : Albert A. Carr, Richard C. Dage, John E. Koerner, Tung Li and Francis P. Miller It is certified that error appears in the above-identified patent and that said Letters Patent is hereby corrected as shown below:

```
At Column 14, line 36, "46.0%" should read -- 46.0 g -- .
At Column 15, line 37, "1.3" should read -- 14.3 --.
At Column 17, line 56, "1.44%" should read -- 1.44 g --.
At Column 18, line 20, "1.99" should read -- 1.9 g --.
At Column 18, line 27, "ethyl-4-" should read
-- ethyl]-4- --.
At Column 19, line 39, "[41-" should read -- [4-[ --.
At Column 19, line 56, "11-hour" should read -- 1-hour --.
At Column 19, line 66, "[11[21" should read -- [1-[2 --.
At Column 20, line 4, "[41-[" should read -- [4-[ --.
At Column 21, line 16, "1-(" should read -- [1-( --.
```

Signed and Sealed this

Nineteenth Day of October, 1993

BRUCE LEHMAN

Attest:

Attesting Officer

Commissioner of Patents and Trademarks